United States Patent [19]

Bauer et al.

[11] Patent Number: 5,780,159
[45] Date of Patent: Jul. 14, 1998

[54] PLASTIC OPTICAL COMPONENTS

[75] Inventors: Monika Bauer; Hartmut Krüger, both of Berlin; Andreas Bräuer, Rabis; Peter Dannberg, Jena, all of Germany

[73] Assignee: Fraunhofer-Gesellschaft zur Forderung der Angewandten Forschung e.V., Munich, Germany

[21] Appl. No.: 656,176

[22] PCT Filed: Sep. 28, 1995

[86] PCT No.: PCT/DE95/01353

§ 371 Date: Jul. 30, 1996

§ 102(e) Date: Jul. 30, 1996

[87] PCT Pub. No.: WO96/11415

PCT Pub. Date: Apr. 18, 1996

[30] Foreign Application Priority Data

Oct. 8, 1994 [DE] Germany .................. 44 35 992.6

[51] Int. Cl.[6] .................. G02B 1/04; C08L 79/04; C08G 73/06
[52] U.S. Cl. .................. 428/422.8; 528/272; 528/363; 528/422; 525/452; 525/534; 427/379; 385/129; 385/131; 359/173

[58] Field of Search .................. 525/534, 452; 427/379; 428/422.8; 359/173; 385/129, 131; 528/422, 272, 363

[56] References Cited

U.S. PATENT DOCUMENTS

| | | | |
|---|---|---|---|
| 4,334,045 | 6/1982 | Wu et al. | 525/439 |
| 4,414,366 | 11/1983 | Wu et al. | 525/439 |
| 4,839,442 | 6/1989 | Craig, Jr. | 528/422 |
| 4,902,752 | 2/1990 | Shimp | 525/420 |
| 5,360,887 | 11/1994 | Tsunemi et al. | 528/97 |
| 5,523,148 | 6/1996 | Afzali-Ardakani et al. | 428/260 |
| 5,527,592 | 6/1996 | Afzali-Ardakani et al. | 428/260 |
| 5,527,593 | 6/1996 | Afzali-Ardakani et al. | 428/209 |
| 5,527,838 | 6/1996 | Afzali-Ardakani et al. | 523/223 |
| 5,529,836 | 6/1996 | Afzali-Ardakani et al. | 428/251 |
| 5,548,034 | 8/1996 | Afzali-Ardakani et al. | 525/390 |
| 5,599,611 | 2/1997 | Afzali-Ardakani et al. | 442/180 |

*Primary Examiner*—P. Hampton-Hightower
*Attorney, Agent, or Firm*—Weingarten, Schurgin, Gagnebin & Hayes LLP

[57] ABSTRACT

The invention concerns optical elements made from polycyanurate resins, which exhibit a refractive index, at 633 nm, in the range from 1.45 to 1.70 and an optical absorption, at 1.3 or 1.55 μm, in the range from 0.1 to 1.0 dB/cm.

17 Claims, No Drawings

PLASTIC OPTICAL COMPONENTS

FIELD OF THE INVENTION

The invention concerns optical elements made of plastic and in particular those made from polycyanurate resins.

BACKGROUND OF THE INVENTION

Polymers are materials of increasing interest for optics, microoptics, integrated optics and microsystems engineering. They are thereby employed in optical components as well as in special optics, such as lenses, prisms, for the fixing of optical systems, as substrate materials for optical coatings and as transparent coating material for mirrors and lenses. Polymers can be utilized for optical fibers and for the generation of waveguide structures. Their general advantage lies in the favorable technological processability and their lower density in comparison with glass.

The application as waveguides, in particular, imposes manifold demands upon the polymer. The refractive index should be as variable as possible and capable of being adapted to certain substrates. In the case of an application in optical communications technology, small material absorptions at 1.3 and 1.55 μm are required. The absorption losses resulting from volume defects (inhomogeneities, microbubbles) must be minimized. In addition to certain engineering requirements, such as coating production and the ability to be structured, particularly the thermal and thermo-mechanical stability, adjusted expansion coefficients and the very low degree of shrinkage are prerequisites for an application of polymers for waveguide structures in integrated optics.

The plastics thus far employed for optical applications are polymethacrylates and polycarbonates. Their refractive index is however, at 1.49 or 1.58, relatively limited and not directly variable. Both polymer classes exhibit an excellent optical transparency but however, due to their chemical structure, are not particularly thermally and thermo-mechanically stable. Polycarbonate, for example, is thus practically unusable at temperatures above 130° C. due to its relatively low glass-transition range.

Other high-performance polymers exhibit glass-transition ranges ($T_g$) of >180° C. Examples of these include polyaryl ether sulfones, polyaryl sulfones, polyaryl ether ketones, polyimides and polyether imides, which, compared with polymethacrylate and polycarbonate, are for the most part however more difficult to process. The application of these high-$T_g$ polymers for optical systems is described is described in various patent documents, for example, in JP-A 61-144,738, JP-A 61-005,986, DE-A 3,915,734, U.S. Pat. No. 4,477,555, EP-A 0,254,275, DE-A 3,429,074, DE-A 3,927,498, DE-A 4,228,853, DE-A 3,636,399. A further disadvantage of these systems is the comparatively high optical absorption at the wavelengths of 1.3 and 1.55 μm relevant to communications technology.

The invention consequently addressed the problem of producing easily workable, thermally and thermo-mechanically stable polymers of variable refractive index and low absorption at 1.3 and 1.55, which are suitable for the manufacture of optical elements, as well as the optical elements manufactured from them.

SUMMARY OF THE INVENTION

This goal is achieved with an optical element of the type initially described, which is produced from a polycyanurate resin.

It was discovered, surprisingly, that polycyanurate resins are particularly well suited for the manufacture of optical elements with the desired properties cited above. These are for the most part known products from conventional polycyanate raw materials, as they are widely used in the plastics industry. Correspondingly, the starting materials, production processes and methods for processing these polycyanurate plastics are known.

DETAILED DESCRIPTION OF THE INVENTION

Particularly suitable for the invented optical elements are polycyanurate resins which are obtained from the compounds shown below.

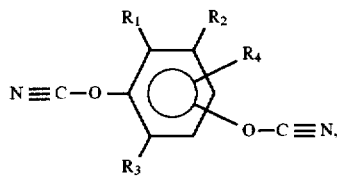

in which $R^1$ through $R^4$, independently of each other, are hydrogen, $C_1$–$C_{10}$-alkyl, $C_3$–$C_8$-cycloalkyl, $C_1$–$C_{10}$-alkoxy, halogen or phenyl, in which case the alkyl or aryl groups can be fluorinated or partially fluorinated,

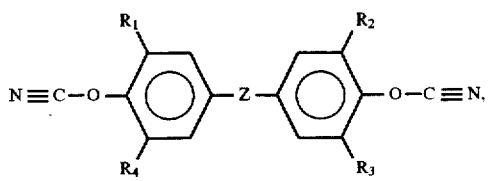

in which Z is a chemical bond, $SO_2$, $CF_2$, $CH_2$, $CH(CH_3)$, isopropyl, hexafluoroisopropyl, $C_1$–$C_{10}$-alkyl, O, $NR^5$, N=N, CH=CH, COO, CH=N, CH=N—N=CH, alkyloxyalkyl with $C_1$–$C_8$-alkyl, S or

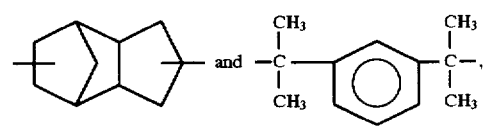

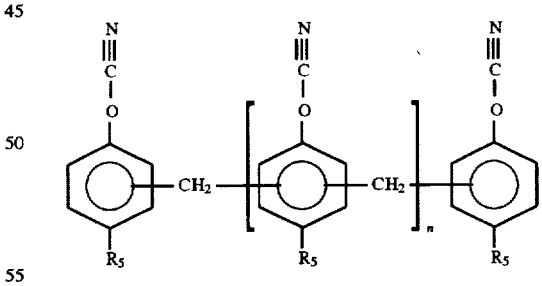

where $R^5$ is hydrogen or $C_1$–$C_{10}$-alkyl and n is 0 through 20; as well as dicyanates of a perhalogenated dihydroxyalkane IV, especially with up to 10 carbon atoms, as well as mixtures of the polycyanates with formulas I through IV.

The properties of the above-cited polycyanurate resins can be favorably influenced, on the one hand, by employing them in mixtures, but, on the other, with phenols, for example, those having structure Va through Vc, in which R is hydrogen and $R^1$ through $R^5$ are defined as above.

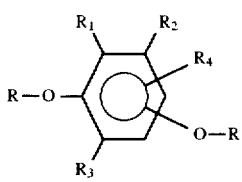
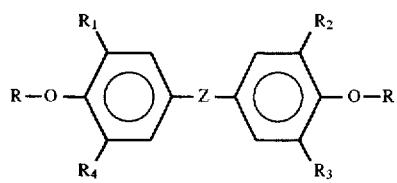
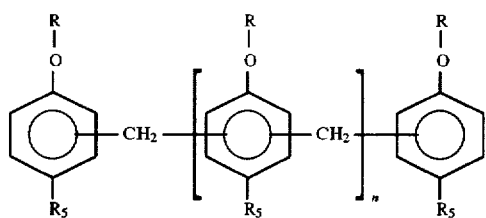

aromatic glycide ethers with structure Va through c, in which R is glycidyl, or glycidyl anilines, for example, with basic structure VIa through c.

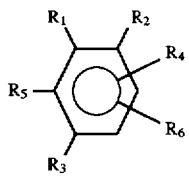
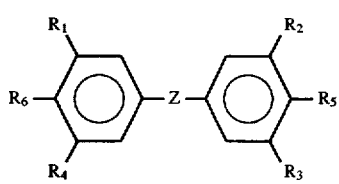
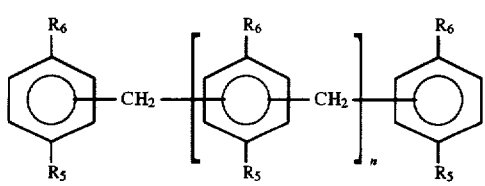

in which $R_6$ is $N(R_7)_2$ with $R_7$ glycidyl, and are converted with complete hardening.

Such coreaction products with phenols, aromatic glycide ethers and glycidyl anilines are likewise well known. It is possible, for example, to obtain polycyanurate resins which, with regard to the polycyanate or polycyanate mixture used, contain from 1 to 60 mol-% of phenol, from 1 to 99 mol-% of glycide ether or from 1 to 99% of glycidyl aniline or mixtures of these components.

The polycyanurate resins employed per the invention have, in particular, a glass-transition temperature $T_g$ of from 100° to 250° C., particularly preferred from 180° to 250° C. Their refractive index at 633 nm lies preferably in the range from 1.45 to 1.70, especially preferred in the range from 1.55 and 1.65.

Per the invention, optical absorptions in the range of from 0.1 to 1.0 dB/cm can be achieved at 1.3 or 1.55 μm.

The polycyanurate resins are suitable for the manufacture of waveguide structures, lenses, prisms, corrected lens systems, optical photoconductive fibers and substrates for optical coatings as well as for the cementing of optical components and for fiber coupling, as well as for numerous other purposes.

The employed polycyanurate resins can be obtained per the invention by employing mixtures of various dicyanates in the polymer-forming reaction. The polycyanurates can be obtained furthermore by the conversion of dicyanates into the invented products in coreactions with phenols, aromatic glycide ethers or glycidyl anilines. The refractive index of the described polycyanurate resins can be varied and adjusted by the mixture of the monomer components in a wider range (1.45 to 1.70). The polymers exhibit thermal stability at up to 250° C. The glass-transition ranges of the invented resins lies between 100° and 250° C., and in particular at >180° C.

The described resins exhibit very low optical losses at 1.3 and 1.55 μm in comparison with other high-Tg polymers, for example, polyimides. The easy processability of the invented materials results from the fact that they can be processed from the solution via spin-coating already in a soluble prepolymer stage, or from the meltings by means of stamping or molding techniques. The polymers exhibit good adhesion to various substrates. Final processing in the layer takes place by thermal hardening.

Subject matter of the invention is furthermore the use of polycyanurate resins, especially those defined in detail above, for the manufacture of optical elements.

The invention is explained in detail by means of the following examples.

EXAMPLE 1

100 g of dicyanate of bisphenol A (compound II with $R_1$ through $R_4$=H, Z=isopropyl) are heated to 180° C., with agitation, under an inert atmosphere. The arising prepolymer is cooled after 350 min. It congeals as a transparent, amorphous, slightly yellowish mass. An OCN conversion of 41% is determined by means of IR spectrography.

The prepolymer is soluble in the conventionally used organic solvents. Films with a thickness range of from 1 to 10 μm are obtained from a 40% solution in hexanone by spin coating. After tempering and hardening of the layer at, finally, 200° C., a refractive index of 1.6095 at 633 nm is obtained. The optical absorption at 1.32 μm was 0.39 dB/cm, at 1.55 μm, 1.1 dB/cm.

EXAMPLE 2

10 g of dicyanate of a substituted bisphenol A (compound II with $R_1$–$R_4$=H, Z=hexafluoroisopropyl) are heated to 180° C. for 70 h until complete hardening is achieved. The result is a transparent, amorphous, colorless body. The OCN conversion is determined by the use of IR spectroscopy.

The castings produced can be processed mechanically. End planes for coupling in the laser beam are obtained by polishing. A refractive index of 1.543 is determined at 663 nm. The optical absorption at 1.32 μm was 0.6 dB/cm, at 1.55 μm, 0.7 dB/cm.

EXAMPLE 3

25 g of a substituted bisphenol A (compound II with $R_1$–$R_4$=CH$_3$, Z=CH$_2$) are heated to 180° C. for 80 h, until complete hardening is achieved. Obtained is a transparent, amorphous, yellowish body. The OCN conversion is detected using IR spectroscopy.

The casting produced can be precessed mechanically. End surfaces for coupling in the laser beam are obtained by polishing. The refractive index determined at 633 nm is 1.579 (1.558 at 1.3 µm). The optical absorption at 1.32 µm was 0.6 dB/cm and 0.6 dB/cm at 1.55 µm.

EXAMPLE 4

7 g of dicyanate of a substituted bisphenol A (compound II with $R_1$–$R_4$=$CH_3$, Z=$CH_2$) and 3 g of dicyanate of bisphenol A (compound II with $R_1$–R=H, Z=isopropyl) are heated to 120° C. for 92 h with the addition of 2% of a catalyst, consisting of 200 parts of phenol and 1 part of Cu(acac)$_2$, until complete hardening. Obtained is a transparent, amorphous, yellowish body. The OCN conversion is ascertained by means of IR spectroscopy.

The resulting casting can be worked by mechanical means. End surfaces for coupling in a laser beam are produced by polishing. The refractive index at 633 nm is found to be 1.592.

EXAMPLE 5

3 g of dicyanate of a substituted bisphenol A (compound II with $R_1$–R=H, Z=hexafluoroisopropyl) and 7 g of dicyanate of bisphenol A (compound II with $R_1$–$R_4$=H, Z=isopropyl) are heated to 120° C. for 92 h with the addition of 2% of a catalyst, consisting of 200 parts of phenol and 1 part of Cu(acac)$_2$, until hardening is complete. The result is a transparent, amorphous, slightly yellowish material. The OCN conversion is determined with IR spectroscopy.

The casting produced can be processed mechanically. End surfaces for coupling in a laser beam are produced by polishing. The refractive index determined at 633 nm is 1.592.

What is claimed is:

1. An optical element comprising plastic, wherein said plastic is a polycyanurate resin.

2. The optical element according to claim 1, wherein said polycyanurate resin is derived from at least one polycyanate selected from the group consisting of

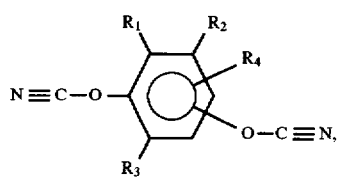

wherein $R^1$ through $R^4$, independently of each other, can be hydrogen, $C_1$–$C_{10}$-alkyl, $C_3$–$C_8$-cycloalkyl, $C_1$–$C_{10}$-alkoxy, halogen or phenyl, in which case the alkyl or aryl groups can be fluorinated or partially fluorinated,

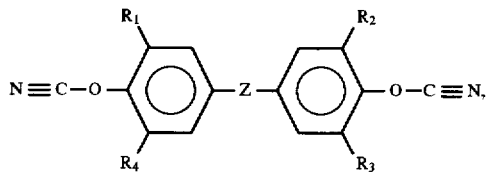

wherein Z is a chemical bond, $SO_2$, $CF_2$, $CH_2$, $CH(CH_3)$, isopropyl, hexfluoroisopropyl, $C_1$–$C_{10}$-alkyl, O, $NR^5$, N=N, CH=CH, COO, CH=N, CH=N—N=CH, alkyloxyalkyl with $C_1$–$C_8$-alkyl, S or

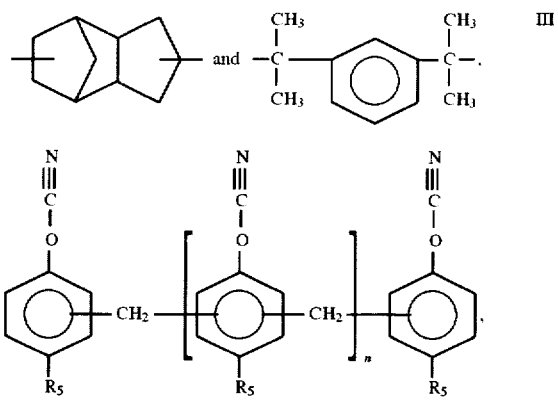

where $R^5$ is hydrogen or $C_1$–$C_{10}$-alkyl and n equals 0–20, and a dicyanate of a perhalogenated dihydroxy alkane IV.

3. The optical element of claim 1 wherein said polycyanurate resin is derived from a bisphenol-A dicyanate.

4. The optical element of claim 1, wherein said polycyanurate resins are coreaction products of the polycyanates with phenols, aromatic glycide ethers or glycidyl anilines.

5. The optical element of claim 4, wherein said polycyanurate resins contain, relative to the polycyanate used, from 1 to 60 mol-% of phenol, from 1 to 99 mol-% of glycidyl ether or from 1 to 99 mol-% of glycidyl aniline.

6. The optical element of claim 1 wherein said polycyanurate resin exhibits a glass-transition temperature of from approximately 100° C. to approximately 250° C.

7. The optical element of claim 1 wherein said optical element has a refractive index, at 633 nm, in the range of from 1.45 to 1.70.

8. The optical element of claim 1 wherein said optical element has an optical absorption, at 1.3 or 1.55 µm, in the range of from 0.1 to 1.0 dB/cm.

9. The optical element of claim 1 wherein said optical element is obtained by spin-coating the dissolved polycyanurate resin.

10. The optical element of claim 1 wherein said optical element is obtained from meltings by molding techniques.

11. Optical element of claim 1 wherein the polycyanurate resin is thermally hardened.

12. The optical element of claim 1 wherein said optical element is an optical device selected from the group consisting of waveguide structures, lenses, prisms, corrected-lens systems, optical photoconductive fibers, substrates for optical coatings, and adhesives for optical components.

13. The optical element of claim 2 wherein the dicyanate of a perhalogenated dihydroxy alkane has up to 10 carbon atoms.

14. The optical element of claim 1 wherein said polycyanurate resin exhibits a glass-transition temperature of from approximately 180° C. to approximately 250° C.

15. The optical element of claim 1 wherein said optical element has a refractive index, at 633 nm, in the range of from 1.55 to 1.65.

16. The optical element of claim 1 wherein said optical element is obtained from meltings by stamping techniques.

17. The optical elements of claim 11 wherein said polycyanurate resin has been thermally hardened in the presence of a catalyst.

* * * * *